United States Patent
Stoppe et al.

(10) Patent No.: US 10,338,368 B2
(45) Date of Patent: Jul. 2, 2019

(54) PHASE CONTRAST IMAGING

(71) Applicant: Carl Zeiss Microscopy GmbH, Jena (DE)

(72) Inventors: Lars Stoppe, Jena (DE); Christoph Husemann, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 83 days.

(21) Appl. No.: 15/506,151

(22) PCT Filed: Aug. 25, 2015

(86) PCT No.: PCT/EP2015/069469
§ 371 (c)(1),
(2) Date: Feb. 23, 2017

(87) PCT Pub. No.: WO2016/030390
PCT Pub. Date: Mar. 3, 2016

(65) Prior Publication Data
US 2017/0276923 A1    Sep. 28, 2017

(30) Foreign Application Priority Data

Aug. 26, 2014 (DE) .................. 10 2014 112 242

(51) Int. Cl.
*G06K 9/00* (2006.01)
*G02B 21/14* (2006.01)
(Continued)

(52) U.S. Cl.
CPC ............. *G02B 21/14* (2013.01); *G02B 21/06* (2013.01); *G06T 7/97* (2017.01); *G06T 2207/10056* (2013.01); *G06T 2207/20212* (2013.01)

(58) Field of Classification Search
CPC ........ G02B 21/14; G02B 21/06; G02B 21/08; G02B 21/36; G02B 21/10; G02B 21/365;
(Continued)

(56) References Cited

U.S. PATENT DOCUMENTS 2,950,648 A  8/1960  Rhodes et al.
5,932,872 A  8/1999  Price
(Continued)

FOREIGN PATENT DOCUMENTS

CN  102998789 A  3/2013
CN  103913860 A  7/2014
(Continued)

OTHER PUBLICATIONS

Bishara et al., "Holographic pixel super-resolution in portable lens-less on-chip microscopy using a fiber-optic array," The Royal Society of Chemestry, Lab Chip 11, 1276-1279 (2011).*
(Continued)

*Primary Examiner* — Jose L Couso
(74) *Attorney, Agent, or Firm* — Murphy, Bilak & Homiller, PLLC

(57) ABSTRACT

An object is illuminated from at least one illuminating direction. For each illuminating direction, an intensity image of the object is captured during the illumination. On the basis of the at least one intensity image, a phase contrast image of the object is generated.

13 Claims, 11 Drawing Sheets

(51) Int. Cl.
*G02B 21/06* (2006.01)
*G06T 7/00* (2017.01)

(58) Field of Classification Search
CPC ............... G02B 21/002; G02B 21/008; G02B 21/0056; G02B 21/0032; G02B 21/088; G02B 21/245; G02B 21/0064; G02B 21/361; G02B 21/125; G02B 21/367; G02B 27/52; G02B 21/0004; G02B 21/0012; G02B 21/0092; G02B 21/02; G02B 21/18; G02B 21/34; G06T 7/97; G06T 7/0012; G06T 2207/10056; G06T 2207/20221; G06T 2207/300246; G06T 2207/10068; G06T 2207/10152; G06T 2207/20208; G06T 5/009; G06T 5/50; Y01S 977/869; Y01S 977/881; G01N 15/1436; G01N 2015/0065; G01N 2015/1006; G01N 2015/144; G01N 21/055; G01N 21/27; G06K 9/00127; G06K 9/00134; G06K 2209/403; H04N 5/2256; H04N 5/23238; G03H 2001/005; A61B 1/00009; A61B 1/00172; A61B 1/04; G01J 9/0215

See application file for complete search history.

(56) References Cited

U.S. PATENT DOCUMENTS

| | | | | |
|---|---|---|---|---|
| 9,892,812 | B2 * | 2/2018 | Zheng | G21K 7/00 |
| 10,162,161 | B2 * | 12/2018 | Horstmeyer | G02B 21/361 |
| 10,168,525 | B2 * | 1/2019 | Kim | G01N 21/6452 |
| 2006/0012871 | A1 * | 1/2006 | Funk | G01J 3/02 |
| | | | | 359/385 |
| 2007/0211460 | A1 | 9/2007 | Ravkin | |
| 2008/0032325 | A1 * | 2/2008 | DiMarzio | G02B 21/0004 |
| | | | | 435/29 |
| 2011/0025837 | A1 | 2/2011 | Vossen et al. | |
| 2014/0098416 | A1 * | 4/2014 | Schmidt | G02B 21/14 |
| | | | | 359/370 |
| 2014/0333997 | A1 | 11/2014 | Oda | |
| 2015/0087902 | A1 * | 3/2015 | Mertz | G02B 21/14 |
| | | | | 600/109 |
| 2016/0210763 | A1 * | 7/2016 | Horstmeyer | G06T 11/006 |
| 2016/0266366 | A1 * | 9/2016 | Chung | G02B 21/0072 |
| 2017/0146788 | A1 * | 5/2017 | Waller | G02B 21/367 |
| 2017/0220000 | A1 * | 8/2017 | Ozcan | G03H 1/0005 |
| 2017/0261419 | A1 * | 9/2017 | Glensbjerg | G01N 15/1436 |

FOREIGN PATENT DOCUMENTS

| | | |
|---|---|---|
| DE | 3540916 A1 | 5/1987 |
| DE | 102009038027 A1 | 2/2011 |
| EP | 2645146 A1 | 10/2013 |
| JP | 2001149348 A | 6/2001 |
| JP | 2008111726 A | 5/2008 |
| JP | 2011229699 A | 11/2011 |
| JP | 2012073591 A | 4/2012 |
| JP | 2014147756 A | 8/2014 |
| WO | 03001165 A1 | 1/2003 |
| WO | 2011020550 A1 | 2/2011 |
| WO | 2013094434 A1 | 6/2013 |
| WO | 2013148360 A1 | 10/2013 |

OTHER PUBLICATIONS

Mehta, Shalin B. et al., "Quantitative phase-gradient imaging at high resolution with asymmetric illumination-based differential phase contrast", Optics Letters vol. 34, No. 13, Jul. 1, 2009, 1924-1926.

* cited by examiner

PHASE CONTRAST IMAGING

TECHNICAL FIELD

The present application relates to a method for generating a phase contrast image of an object and to a corresponding optical device. In particular, the present application relates to techniques in which the object is illuminated sequentially from at least two illuminating directions and the phase contrast image is generated on the basis of corresponding intensity images.

BACKGROUND

In the optical imaging of objects, it is often desirable to generate what is known as a phase contrast image. In the phase contrast image, at least part of the image contrast is caused by a phase shift of the light through the object depicted. This allows in particular objects that bring about no attenuation or only a slight attenuation of the amplitude of the light, but a significant phase shift (phase objects) to be depicted with comparatively higher contrast. Typically, biological specimens as an object in a microscope may bring about a greater change in phase than a change in amplitude of the electromagnetic field.

Various techniques for phase contrast imaging are known, for instance darkfield illumination, oblique illumination, differential interference contrast (DIC) or Zernike phase contrast. Further techniques would be for example the schlieren (knife-edge) method or helical phase contrast.

Such aforementioned techniques have various disadvantages or restrictions. For instance, in the case of the DIC technique, the Zernike technique, the schlieren method and the helical phase contrast, it is typically necessary in comparison with conventional amplitude imaging to provide additional optical elements between the specimen and the detector in the region of what is known as the detection optics. This may lead to restrictions in the structural design, in particular in the case of microscopes of a modular construction. Costs are typically increased. In the case of thin specimens, with darkfield illumination typically only few photons contribute to producing the image, which may lead to noisy images of inferior quality. A subsequent evaluation or analysis of the images may not be possible, or only to a restricted extent. Oblique illumination typically leads to an unsymmetrical increase in contrast, which in turn may bring about reduced quality of the images.

SUMMARY

There is therefore a need for improved techniques of phase contrast imaging. In particular, there is a need for such techniques that make a robust and simple construction of the optical device possible and make good image quality possible.

This object is achieved by the features of the independent claims. The dependent claims define embodiments.

According to one aspect, the present invention relates to a method for generating a phase contrast image of an object with an optical device. The method comprises sequentially illuminating the object from at least two illuminating directions. The method also comprises, for each illuminating direction, capturing an intensity image of the object during the illumination from the respective illuminating direction. The method also comprises combining original images to obtain a phase contrast image of the object. The original images are based on the captured intensity images. The at least two illuminating directions are in each case assigned to a pair of illuminating directions.

In other words, the at least two illuminating directions may in each case form pairs or be arranged as pairs. In this case it may be possible that an illuminating direction is only ever assigned to one pair. It would however also be possible that at least some of the illuminating directions are assigned to multiple pairs.

For example, the optical device may be a microscopy device. The phase contrast image may therefore depict the object magnified. The at least two illuminating directions may in particular form different angles with that axis of the optical device along which an idealized light beam undergoes no deflection or only a slight deflection (optical axis). In a simple implementation, for example, the intensity images of the object from any two or three or more illuminating directions that form a different angle with the optical axis may be combined. Then, a specific phase contrast component may already be obtained in the phase contrast image.

While the intensity images typically do not have any phase contrast, or no significant phase contrast, the phase contrast image that has a significant phase contrast component can be generated by the combining of the original images. In particular in comparison with other conventional techniques of phase contrast imaging, with the method described in the present case the effect of a particularly simple implementation of the phase contrast imaging on the one hand and the effect of a particularly simple and consequently low-cost and robust configuration of the optical device on the other hand can be achieved. In particular, it may be possible to use different conventional microscopy devices according to the technique described here without any modification of a detection optics being necessary.

Various criteria may apply for the assignment of two illuminating directions to a pair. For example, geometrical criteria of the illuminating directions of a pair may apply, for instance with respect to the optical axis; in this way it may for example be possible to generate a particularly high phase contrast component in the phase contrast image. For example, the illuminating directions of a pair could be arranged symmetrically with respect to the optical axis and/or a plane that contains the optical axis. It would however alternatively or additionally also be possible that a point in time of the illumination and capture is taken into consideration as an alternative or additional criterion for two illuminating directions to belong to a pair; for example, those illuminating directions for which the respective intensity image is captured directly one after the other or soon one after the other may form a pair; in such a way for example a certain robustness with respect to movement artefacts could be achieved. Generally, a subsequent evaluation for generating the phase contrast image may also be taken into consideration as an alternative or additional criterion for two illuminating directions to belong to a pair; for example, a single original image could always be generated for the two intensity images of a pair by combining these intensity images.

It would be possible that the two illuminating directions of a pair form correlating angles with the optical axis. Correlating angles mean for example: angles that are substantially the same or angles that are substantially the same in absolute terms; substantially may be characterized in particular with respect to technical limitations on the accuracy, such as for example systematic or statistical errors in the capture of the intensity images by the optical device and/or structurally caused limitation of an illuminating device of the optical device. As long as angles which, though different in absolute terms, are the same for example within the accuracy of the optical device are implemented, this can satisfy such a criterion of substantially the same angles. Such criteria apply hereinafter to corresponding indications of angles and/or other properties of illuminating directions of the optical device.

It may be helpful for the description of geometrical properties of the illuminating directions to describe the illuminating directions by an illumination vector. The illumination vectors may be defined with respect to an origin of the optical device, for instance with respect to the object and/or a point of intersection of a focal plane with the optical axis. A length of the illumination vectors may for example correspond to an amplitude of the illumination from the respective illuminating direction; in the subsequent discussion of the orientation of various illumination vectors, it may be superfluous to take a length of the illumination vectors into consideration. The angle that an illumination vector forms with the optical axis may then correspond to the angle of the respective illuminating direction.

For example, it may be desirable that illumination vectors of a pair of illuminating directions form an angle with one another that is greater than 10°, preferably greater than 20°, particularly preferably greater than 40°. It would alternatively or additionally also be possible that illumination vectors of a pair of illuminating directions in each case form an angle with the optical axis that is greater than 5°, preferably greater than 10°, particularly preferably greater than 20°. In this way it can be achieved that a difference vector between the two illumination vectors of a pair of illuminating directions has a significant component perpendicularly to the optical axis; this may increase the phase contrast in the phase contrast image particularly strongly.

In particular, it may be possible that the illumination vectors of two illuminating directions of a pair of illuminating directions can be transformed into one another by rotation about the optical axis of the optical device by an angle of greater than 25°, preferably of greater than 50°, particularly preferably of greater than 85°. As a result, the difference vector becomes particularly great. The two illuminating directions of a pair of illuminating directions may also be arranged in such a way that associated illumination vectors can be transformed into one another by rotation about the optical axis by an angle of 160° to 200°, advantageously of 175° to 185°, particularly advantageously of 180°. It would also be possible that the associated illumination vectors can be transformed into one another by rotation about the optical axis by an angle of 70° to 110°, advantageously of 85° to 95°, particularly advantageously of 90°. In other words, the two illumination vectors of a pair of illuminating directions may lie in one plane and be arranged symmetrically or substantially symmetrically with respect to the optical axis. The optical axis may lie in this plane (be contained by this plane), for example if a rotation by 180° transforms the two illumination vectors into one another. In this way, a comparatively great phase contrast component can be obtained in the phase contrast image, since the two illuminating directions of a pair are in such a way arranged complementarily in relation to one another.

It may generally be desirable to use a greater number of illuminating directions to obtain the phase contrast image. In particular, with appropriate arrangement of the various illuminating directions, the phase contrast component in the phase contrast image may increase. For example, it would be possible to take multiple pairs of illuminating directions into consideration. For example, it would be possible to illuminate the object sequentially from 2 or 4 or 6 or 8 illuminating directions or more illuminating directions. For example, it would be possible that a first pair of illuminating directions determines a first difference vector of associated illumination vectors. A second pair of illuminating directions may correspondingly determine a second difference vector of associated illumination vectors. The first and second difference vectors may form an angle with one another, for example of 70° to 110°, advantageously of 85° to 95°, particularly advantageously of 90°.

It would correspondingly also be possible that a first plane is defined by the illumination vectors of a first pair of illuminating directions. A second plane may for example be defined by the illumination vectors of a second pair of illuminating directions. The first plane and the second plane may for example form an angle with one another of 70° to 110°, advantageously of 85° to 95°, particularly advantageously of 90°. The planes may for example be defined by the respective illumination vectors lying in the plane. It would also be possible that the planes are defined by a normal vector, which is oriented parallel to a difference vector of the respective illumination vectors; the optical axis may lie in the plane.

In this way, difference vectors of the illumination vectors of the two pairs of illuminating directions may therefore form a comparatively great angle with one another of up to 90°; as a result, the phase contrast in the phase contrast image can be increased along various image directions. For example, a phase contrast component in the phase contrast image may be particularly great along those image directions for which illumination vectors of a pair of illuminating directions have a component perpendicularly to the optical axis. In particular, a phase contrast component in the phase contrast image may be particularly great along those directions for which the difference vector of the illumination vectors of a pair of illuminating directions has a component perpendicularly to the optical axis. For this reason, it may be desirable to use complementarily and/or symmetrically arranged illuminating directions. In order to generate an isotropic phase contrast in the phase contrast image, it may be desirable that the illuminating directions form uniformly distributed angles with the optical axis.

It would for example be possible to generate multiple phase contrast images that have a directionally dependent phase contrast. For example, a first phase contrast image could have a significant phase contrast along a first image direction and a second phase contrast image could have a significant phase contrast along a second image direction, the first and second image directions forming an angle with one another, for example an angle of 70° to 110°, advantageously of 85° to 95°, particularly advantageously of 90°.

According to the present aspect, the method for generating the phase contrast image may for example be used for a first pair of illuminating directions and be used for a second pair of illuminating directions, whereby the first phase contrast image and the second phase contrast image are generated. Difference vectors of the respective illumination vectors of the first pair and of the second pair may form an angle with one another, for example an angle of 70° to 110°, advantageously of 85° to 95°, particularly advantageously of 90°. It can then be achieved that the first phase contrast image has a significant phase contrast along a different image direction than the second phase contrast image. A directionally dependent phase contrast can be generated. This may make a particularly high information content possible in a subsequent evaluation or analysis of the phase contrast images.

It would correspondingly be possible that illumination vectors of a first pair of illuminating directions can be transformed into one another by mirroring at a first plane, which contains the optical axis. Illumination vectors of a second pair of illuminating directions may be transformed into one another by mirroring at a second plane, which contains the optical axis and is perpendicular to the first plane. This may mean that difference vectors of illumination vectors of a pair of illuminating direction form an angle with one another of substantially 90°. Then, the phase contrast image can have a high phase contrast along different directions.

Various geometrical arrangements of the at least two illuminating directions have been mentioned above. In principle, a wide variety of illuminating devices may be used to carry out the illumination of the object with the various illuminating directions. For instance, a scanning mirror may be used for example in a field stop plane of the illuminating device. An adaptive component could also be used in an aperture stop or illumination pupil of the illuminating device; for example, the illuminating device according to German patent application 10 2014 101 219.4 could be used. It would also be possible that the illuminating device comprises a light-emitting diode array. For example, the light-emitting diodes of the light-emitting diode array may be arranged according to a Cartesian grid, it being possible for individual cells of the grid to be square or rectangular. Other grids may also be implemented, for instance hexagonal grids, etc. It would for example also be possible that the light-emitting diode array comprises one or more rings of light-emitting diodes, for example with different radii. It is then possible for example by activating a specific light-emitting diode of the light-emitting diode array that is at a specific distance from the optical axis to implement a specific illuminating direction.

Thus, the method may for example comprise for each pair of illuminating directions: activating a first light-emitting diode of the light-emitting diode array to illuminate the object from a first illuminating direction; and activating a second light-emitting diode of the light-emitting diode array to illuminate the object from a second illuminating direction. The light-emitting diode array may for example have n rows of light-emitting diodes and m columns of light-emitting diodes. The first light-emitting diode may correspond to the i;j light-emitting diode of the light-emitting diode array; correspondingly, the second light-emitting diode may be selected from the following group: n−i+1; j light-emitting diode; i; m−j+1 light-emitting diode; n−i+1; m−j+1 light-emitting diode.

i may therefore denote a row index of the light-emitting diode array, and consequently be chosen in the range from 1 to n. j may therefore denote a column index of the light-emitting diode array, and consequently be chosen in the range from 1 to m. If it is a square light-emitting diode array, then m=n.

By activating the light-emitting diodes symmetrically in pairs in such a way, the special geometrical relationship discussed above can be implemented in particular: in the case where the second light-emitting diode is chosen according to n−i+1; j or i; m−j+1, a scenario as described above with respect to the third plane may arise; in the case where a second light-emitting diode is chosen according to i; m−j+1 and a third light-emitting diode is chosen according to n−i+1; j, the case described above case of the third and fourth planes may arise; in the case where the second light-emitting diode is chosen according to n−i+1; m−j+1, the case described above of transforming the illuminating directions by rotation about the optical axis by an angle of substantially 180° may arise.

As explained above, generally a different number and arrangement of illuminating directions may be chosen. In particular, pairs of illuminating directions that are in a specific geometrical relationship with one another may be chosen. In such a case, generally a pair can increase a phase contrast of the structure of the lines in the phase contrast image perpendicularly to a connecting line within the pair, i.e. parallel to the difference vector; the connecting line within the pair may in this case correspond to a change in difference of the illumination vectors. It may generally be desirable for the method for generating the phase contrast image to be carried out particularly rapidly; this can typically be achieved already with one or two pairs of illuminating directions; as long as for example two pairs of illuminating directions are used, the two pairs can be rotated by 90°. Generally, a more uniform increase in the phase contrast in the generated phase contrast image can be achieved with a higher scanning rate of the space of the illuminating directions; this means that generally a greater number of pairs of illuminating directions, which are for example distributed uniformly or randomly over the corresponding space of illuminating directions, may be desirable. Differently oblique illuminating directions may in particular increase the plasticity of the phase contrast image. While such illuminating directions that form a finite angle with the optical axis have been discussed in particular above, it is generally also possible to use that illuminating direction that is parallel to the optical axis. Apart from the influence of a number of illuminating directions considered or intensity images used on the phase contrast of the phase contrast image, the using of a relatively great number of illuminating directions may also be desirable with regard to a signal-to-noise ratio. Generally, the phase contrast image may be less affected by noise the more intensity images are used to obtain the phase contrast image. Signal noise may be caused for example by photon noise and/or camera noise of the individual intensity images.

While techniques that concern the type and/or arrangement of the illuminating directions have primarily been described above, techniques that concern the generating of the phase contrast image on the basis of the captured intensity images are primarily described below.

In a simple implementation, the original images may correspond to the intensity images. The original images may however also be obtained from the intensity images by using certain post-processing steps; as a result, it may for example be possible to generate the phase contrast image with a comparatively high phase contrast and/or a comparatively high signal-to-noise ratio. For example, the original images may be obtained by applying an operator to the captured intensity images. The operator may for example be selected from the following group: absolute value; square; root; sign reversal; smoothing of pixels; aberration correction of pixels; and normalizing to a mean value of pixel values of the respective intensity image. For example, the normalizing to the mean value may comprise: subtracting a mean value of pixel values of the respective intensity image from each pixel value of the respective intensity image to obtain a corresponding original image.

It is generally possible that an original image is determined for each intensity image, that is to say there is a 1:1 assignment between intensity images and original images. It would however also be possible that multiple intensity images are combined to form an original image. For example, the original image may therefore be determined by combining multiple intensity images.

It would for example be possible that the method also comprises: combining those intensity images that correspond to a pair of illuminating directions to form in each case an original image. In particular for the case where the illuminating directions that are assigned to a pair satisfy specific geometrical relationships, in this way a particularly high phase contrast component can be obtained in the generated phase contrast image. The original images obtained in this way may then in turn be combined in order to generate the phase contrast image.

By combining two intensity images of a pair of illuminating directions to form in each case an original image, particularly great flexibility can be ensured in the combining operation. In particular, it may for example be possible in the combining operation to weight individual images to a greater or lesser degree. In this way it may be possible for example to compensate for certain optical effects that may occur due to an angle that the respective illuminating direction forms with the optical axis. For example, a medium intensity of an intensity image captured at a greater (smaller) angle that the respective illuminating direction forms with the optical axis may be smaller (greater). It may be possible to compensate for such effects by suitable combining techniques. Increased flexibility can be achieved in particular in comparison with techniques in which a relatively great number of intensity images and/or original images are combined at one time.

For example, the combining of the intensity images could comprise a subtraction of the respective intensity images to obtain the original images. The combining of the original images may comprise an addition of the absolute values of the original images to generate the phase contrast image.

Generally, the combining technique is therefore not particularly restricted. The various original images may for example be subtracted or added; the same applies correspondingly to the intensity images, as long as they are combined to obtain an original image.

For example, the combining of the original images may comprise a weighted summation of the original images. In the weighted summation, each original image may be allocated a weighting factor. The method may for example also comprise for each original image: determining the weighting factor on the basis of an angle that the corresponding illuminating direction forms with the optical axis of the optical device. For example, the weighting factor may be determined to be all the greater (smaller) the greater (smaller) the angle of the corresponding illuminating direction with the optical axis is. Typically, a signal-to-noise ratio of the respective intensity image may thus be smaller (greater) for greater (smaller) angles of the respective illuminating direction with the optical axis—with the amplitude of the corresponding illumination field remaining the same. In this way it is possible for example for a smaller signal-to-noise ratio in the intensity images to be compensated for greater angles of the illuminating direction. For example, the weighting factor may be determined in such a way that a component of the respective illumination vectors parallel to the optical axis assumes a predetermined length, for example the same length for the various illuminating directions.

By carrying out a weighted summation, it may therefore be possible to take into consideration in the combining operation the various influences of the various illuminating directions or of the various pairs of illuminating directions on the respective intensity images. In this way it may be possible to generate a particularly high-quality phase contrast image—for example in particular in comparison with techniques that combine without distinction various illuminating directions to the right and left of the optical axis.

By means of the aforementioned techniques, it may be superfluous to use further optical elements, such as are used for example in conventional phase contrast imaging techniques. In particular, for example, the illuminating with light may be performed in such a way that the light in the optical path of the optical device between the object and a detector does not pass through any elements that are selected from the following group: pole filter; prism; Wollaston prism; phase ring; grayscale filter. A simplified construction of the optical device can thus be achieved in particular in relation to established previously known techniques of phase contrast imaging, such as for example the DIC technique or the Zernike technique.

This may lower operating costs or reduce susceptibility to faults during operation. Furthermore, it may be superfluous for the present method to use particularly coherent light and/or monochromatic light. For example, the illuminating may be performed with incoherent light. In particular, the illuminating of the object may also be performed with white light, which has a significant spectral width. It may also be possible in this way to make the illuminating device of the optical device comparatively low-cost and robust with respect to faults.

In particular, it may be superfluous to perform modifications with respect to the conventional intensity imaging within the detection optics, i.e. between the object and the detector. This may allow previously described techniques to be used in various microscopes. In particular in comparison with the DIC technique, the Zernike technique and other techniques that intervene in the detection optics, such as for example the schlieren method or helical phase contrast, this has the effect of increased flexibility in use. Furthermore, by combining the phase intensity images to generate the phase contrast image, it can be ensured that even thin specimens appear bright in the phase contrast image—this is advantageous in particular in comparison with phase contrast imaging techniques that are based on darkfield illumination. With suitable choice of the illuminating directions, as described above, it can also be ensured that the phase contrast in the generated phase contrast image is increased uniformly or deliberately in different directions. In particular in comparison with the conventional technique of oblique illumination, in this way an improved phase contrast image can be generated. Furthermore, it is possible by means of the techniques described above to choose a stop of the illuminating device that is the same or substantially the same as a stop of the detection device of the optical device; in particular, it may be superfluous that the illumination stop is greater than the detection stop. In this way it is possible for example to obtain a simplified construction of the optical device in comparison with darkfield illumination. By means of the techniques described above, it may also be possible to carry out a quantitative phase reconstruction, in which a contrast of the phase contrast image generated is proportional to a phase shift. In particular in comparison with conventional techniques operating in the image space, such as for example darkfield illumination, oblique illumination, the DIC technique, Zernike phase contrast, the schlieren method or helical phase contrast, in this way a particularly meaningful phase contrast image can be generated. Further techniques, such as for example Fourier ptychography, that operate in the spatial frequency space instead of in the image space—as in the present case—typically require more extensive and more complex computing steps than the present techniques, which operate in the image space. Therefore, in particular in the case of real-time applications or those applications in which rapid generation of the phase contrast image is desired, the application of the aforementioned technique may be particularly desirable.

Generally, the combining of the original images or the generating of the original images from the intensity images is flexibly adaptable. Thus, for example, the weighting factors in a weighted summation of the original images may for example be adapted specimen-dependently or by a user. This allows for example a phase contrast of the generated phase contrast image that is optimized for a specific specimen being investigated to be made possible; in particular, this may be possible without having to perform intervention in the hardware of the optical device. This may allow a simplified adaptation of the imaging parameters for generating the phase contrast image, in particular in comparison with conventional techniques of phase contrast imaging; in particular, such imaging parameters can be adapted more robustly and more reliably. It may also be possible to adapt the imaging parameters retrospectively, i.e. after illuminating and capturing the object. This may increase flexibility in the imaging. Furthermore, items of amplitude information of the depicted object are taken into consideration in the resultant image. This may be an advantage in particular in comparison with the previously known technique of darkfield illumination.

According to a further aspect, the present application relates to an optical device. The optical device is designed to generate a phase contrast image of an object. The optical device comprises an illuminating device, which is designed to illuminate the object from at least two illuminating directions. The at least two illuminating directions are assigned in each case to a pair of illuminating directions. The optical device comprises a detector, which is designed to capture an intensity image of the object for each illuminating direction during the illumination from the respective illuminating direction. The optical device also comprises a computing unit, which is designed to combine original images based on the captured intensity images in the image space to generate a phase contrast image of the object.

The illuminating device may comprise a light-emitting diode array. The light-emitting diodes of the light-emitting diode array may illuminate the object with incoherent light.

The optical device according to the presently discussed aspect of the application may be designed to carry out the method for generating a phase contrast image according to a further aspect of the present application.

Effects that are comparable with the effects that can be obtained for the method for generating a phase contrast image with a further aspect of the present invention can be achieved for such an optical device.

According to a further aspect, the present application relates to a method for generating a phase contrast image of an object with an optical device. The method comprises illuminating the object from an illuminating direction. The illuminating direction forms a finite angle with the optical axis of the optical device. The method also comprises capturing an intensity image of the object during the illumination from the illuminating direction. The method also comprises processing the intensity image to generate the phase contrast image. The processing of the intensity image comprises the rescaling of the phase contrast image.

It may therefore be possible to generate a phase contrast image on the basis of only a single intensity image. By means of such techniques, it may be possible to generate the phase contrast image particularly rapidly. This may for example have advantages with respect to moved specimens. It may also be possible to illuminate the object with comparatively low light exposure. Furthermore, such a technique may have the effect of reduced computing capacities when generating the phase contrast image. Thus, it may for example be superfluous to process multiple intensity images or a relatively great number of intensity images. In this way, generating the phase contrast image by post-processing can take place particularly rapidly.

It would also be possible that the method also comprises: repeatedly carrying out the capturing and processing of the intensity image for various illuminating directions and combining the phase contrast images thus generated. In this way it may be possible for example to generate a particularly high phase contrast component in the phase contrast image. It can also be achieved that a signal-to-noise ratio in the phase contrast image obtained in this way is particularly high.

Generally, various techniques may be used for the rescaling. For example, the rescaling may comprise: subtracting a mean value of pixel values of the intensity image from pixel values of the intensity image. For example, the mean value of all the pixel values may in each case be subtracted from each pixel value of the intensity image. The pixel values may for example be proportional to a brightness of the object at the position depicted by the respective pixel.

It is generally possible that the processing of the intensity image comprises still further steps, for example smoothing steps, etc. It would for example be possible that the processing of the intensity image also comprises the applying of an absolute value operator to the rescaled intensity image. For example, the applying of the absolute value operator may have the effect that, for each pixel, the respective pixel value with a positive sign is output.

According to a further aspect, the application relates to an optical device, which is designed to generate a phase contrast image of an object. The optical device comprises an illuminating device, which is designed to illuminate the object from an illuminating direction. The illuminating direction forms a finite angle with the optical axis of the optical device. The illuminating device also comprises a detector, which is designed to capture an intensity image of the object during the illumination from the illuminating direction. The optical device also comprises a computing unit, which is designed to process the intensity image to generate the phase contrast image. The processing comprises the rescaling of the phase contrast image.

For example, the optical device according to the presently discussed aspect may be designed to carry out a method for determining a phase contrast image according to a further aspect of the present invention.

Effects that are comparable with the effects that can be achieved for a method for determining a phase contrast image according to a further aspect of the present invention can be achieved for such an optical device.

The features presented above and features described below may be used not only in the corresponding explicitly presented combinations, but also for the combinations on their own without departing from the scope of protection of the present invention. In particular, it may be possible to combine various features that have been described above with reference to aspects in the case of which the phase contrast image is generated on the basis of one or multiple intensity images.

BRIEF DESCRIPTION OF THE DRAWINGS

The properties, features and advantages of this invention that are described above and the manner in which they are achieved become clearer and more easily understandable in conjunction with the following description of the exemplary embodiments, which are explained in more detail in conjunction with the drawings.

DETAILED DESCRIPTION OF EMBODIMENTS

Figure 1:
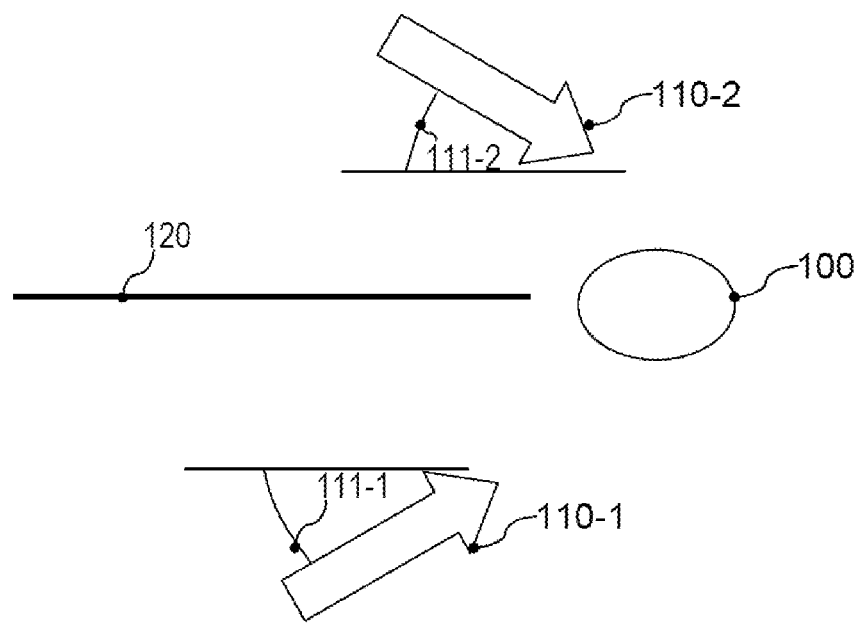
FIG. 1 illustrates two-dimensionally the illuminating of an object from two different illuminating directions.

The present invention is explained in more detail below on the basis of preferred embodiments with reference to the drawings. In the figures, the same reference signs denote the same or similar elements. The figures are schematic representations of various embodiments of the invention. Elements depicted in the figures are not necessarily shown to scale. Rather, the various elements depicted in the figures are reproduced in such a way that their function and general purpose become comprehensible to a person skilled in the art. Connections and couplings between functional units and elements that are depicted in the figures may also be implemented as an indirect connection or coupling. A connection or coupling may be implemented in a wired or wireless manner. Functional units may be implemented as hardware, software or a combination of hardware and software.

Techniques for generating a phase contrast image by means of an optical device are explained below. These techniques are based on a processing or post-processing of one or multiple intensity images of an object that are captured for specific illuminating directions. In one scenario, the phase contrast image may be generated on the basis of a single intensity image. In a further scenario, the phase contrast image may be generated on the basis of multiple intensity images; by combining original images that are based on intensity images, the phase contrast can be obtained in the phase contrast image. In such a scenario, the illuminating directions may in particular be arranged as pairs and in each case the intensity images that correspond to a pair of illuminating directions be combined to form an original image. Subsequently, the original images obtained in this way may be combined to generate the phase contrast image.

The phase contrast of the phase contrast image may be controlled by suitable choice of the illuminating directions. In particular, a geometrical relationship of those illuminating directions that are assigned to a pair may make a specific contribution to the phase contrast. For example, two illuminating directions of a pair of illuminating directions may form correlating angles with the optical axis of the optical device. The correlating angle may for example mean that the two illuminating directions of a pair are symmetrical with respect to the optical axis or in any event form angles of the same absolute value with it. By means of such approaches it is possible for example to generate deliberately a phase contrast that is isotropic or anisotropic over various image directions of the phase contrast image. The phase contrast may also be determined quantitatively, as long as the illuminating direction and possibly further parameters of the respective illumination fields, such as amplitude, etc., are known. Generally, it may be desirable that two illuminating directions of a pair of illuminating directions form an angle with one another that is as great as possible, for example greater than 10° or greater than 20° or greater than 40°. It may also be desirable that a first illuminating direction of a pair of illuminating directions forms a first angle with the optical axis that is for example greater than 5° or greater than 10° or greater than 20°. It may also be desirable that a second illuminating direction of a pair of illuminating directions forms a second angle with the optical axis that is for example greater than 5° or greater than 10° or greater than 20°. Such a comparatively great angle between the illuminating directions of a pair or between the illuminating directions and the optical axis allows a comparatively great phase contrast component to be obtained in the phase contrast image.

The present techniques therefore allow phase contrast images to be generated from the intensity images by suitable processing of the intensity images, i.e. after the actual capture. It is not necessary to provide further optical elements in the region of a detector of the optical device. The illuminating with light may be performed in particular in such a way that the light in the optical path of the optical device between the object and the detector does not pass through any elements selected from the following group: pole filter; prism; Wollaston prism; phase ring; grayscale filter. A simplified and particularly robust construction of the optical device can in this way be achieved in particular in comparison with established techniques of phase contrast imaging, such as for example the DIC technique. The light may have a significant spectral bandwidth and does not have to satisfy any particular coherence criterion.

In FIG. 1, firstly a one-dimensional view of a first illuminating direction 110-1 and a second illuminating direction 110-2 is represented. Also represented in FIG. 1 is the optical axis 120, and also the illuminated object 100. As can be seen from FIG. 1, the first illuminating direction 110-1 forms a first angle 111-1 with the optical axis 120. Furthermore, the second illuminating direction 110-2 forms a second angle 111-2 with the optical axis 120. In particular, the first illuminating direction 110-1 and the second illuminating direction 110-2 are arranged symmetrically with respect to the optical axis 120. The angles 111-1, 111-2 are the same in absolute terms (as long as the value of the angle is counted from zero upward starting from the optical axis 120; though, depending on the direction, provided with an algebraic sign).

For better geometrical description of the illuminating direction 110-1, 110-2, it is possible to resort to the illumination vectors. The illumination vectors may end in the object 100 and may form an angle with the optical axis 120 that corresponds to the angle 111-1, 111-2 of the respective illuminating device 110-1, 110-2.

Figure 2A:
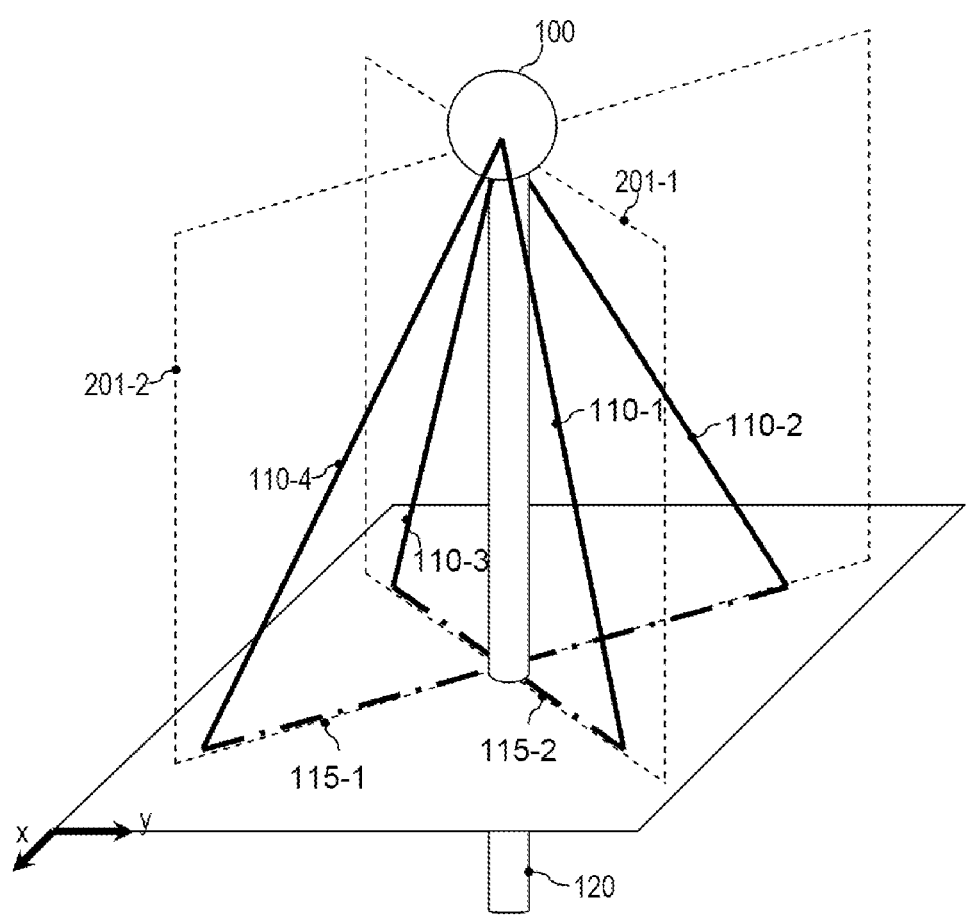
FIG. 2A illustrates three-dimensionally the illuminating of an object from four illuminating directions, two illuminating directions in each case forming a pair.

Such a scenario is represented three-dimensionally in FIG. 2A. In FIG. 2A, 4 illuminating directions 110-1-110-4 are represented by means of illumination vectors; illuminating directions 110-1-110-4 form the same angles with the optical axis 120. A first illuminating direction 110-1 may be transformed into a third illuminating direction 110-3 by rotation about the optical axis 120 by an angle of 180°. Correspondingly, the first illuminating direction 110-1 and the third illuminating direction 110-3 and also the optical axis 120 lie in a first plane 201-1 (represented in FIG. 2A by dashed lines). The first illuminating direction 110-1 and the third illuminating direction 110-3 form a pair of illuminating directions. For example, associated intensity images of the first and third illuminating directions 110-1, 110-3 may be combined to form an original image, for example by subtraction or addition of these intensity images.

It can also be seen from FIG. 2A that a second illuminating direction 110-2 can be transformed into a fourth illuminating direction 110-4 by a rotation about the optical axis 120 of 180°. The second illuminating direction 110-2, the fourth illuminating direction 110-4 and the optical axis 120 lie in a second plane 201-2 (represented in FIG. 2A by dashed lines). For example, associated intensity images of the second and fourth illuminating directions 110-2, 110-4 may be combined to form an original image. The two original images obtained in this way may in turn be combined to generate a phase contrast image, for example by subtraction or addition of these intensity images. The phase contrast image may for example be arranged along the x and y directions indicated in FIG. 2A.

The first plane 201-1 of the first pair of illuminating directions 110-1, 110-3 and the second plane 201-2 of the second pair of illuminating directions 110-2, 110-4 form an angle with one another of 90°. Also represented in FIG. 2A is a connecting line or a first difference vector 115-1 of the illumination vectors of the first pair of illuminating directions 110-1, 110-3. A second difference vector 115-2 of the illumination vectors of the second pair of illuminating directions 110-2, 110-4 is also represented. It can be seen from FIG. 2A that these difference vectors 115-1, 115-2 also form an angle with one another of 90°, to be specific corresponding to the first and second planes 201-1, 201-2. Typically, the first pair of illuminating directions 110-1, 110-3 increases the phase contrast in the phase contrast image perpendicularly to the corresponding difference vector 115-1. Correspondingly, the second pair of illuminating directions 110-2, 110-4 increases the phase contrast in the phase contrast image perpendicularly to the corresponding difference vector 115-2. Since, in the scenario of FIG. 2A, the two difference vectors 115-1, 115-2 form an angle with one another of 90°, i.e. are distributed uniformly over the space of the illuminating directions 110-1-110-4, a comparatively isotropic phase contrast can be generated in the phase contrast image along the various image directions. It would be possible for example by taking into consideration further illuminating directions (not shown in FIG. 2A) that form further angles with the optical axis 120 to generate increased isotropy of the phase contrast along various image directions of the phase contrast image.

Figure 2B:
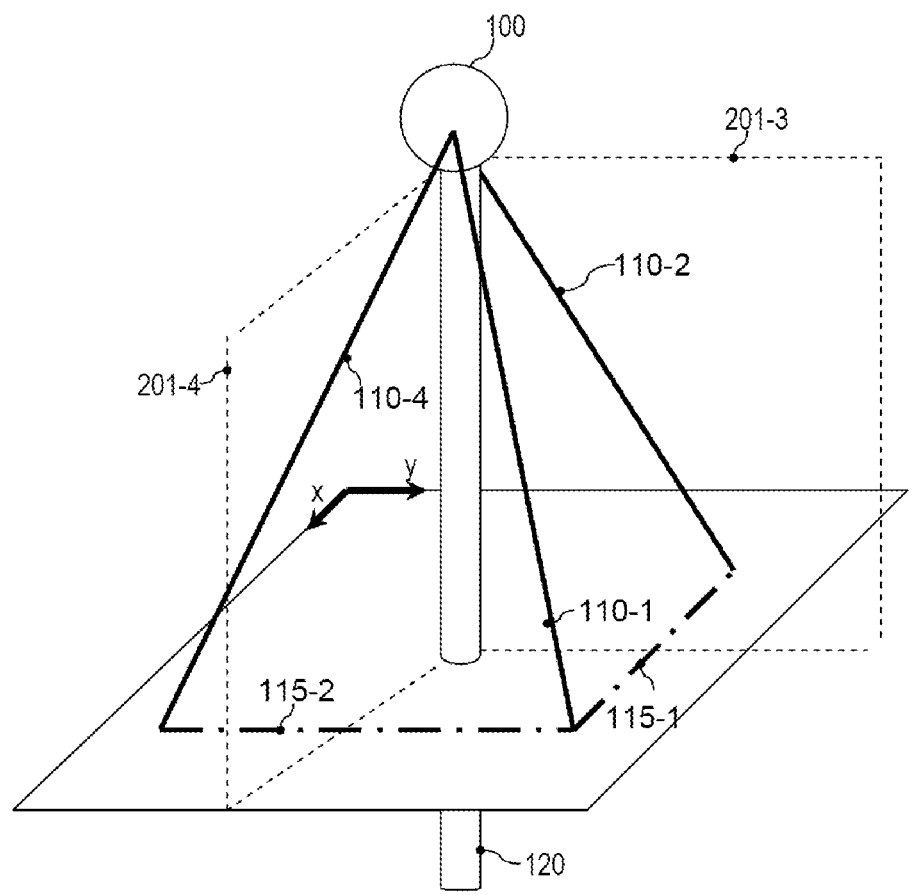
FIG. 2B illustrates three-dimensionally the illuminating of an object from three different illuminating directions, two illuminating directions in each case forming a pair.

In the scenario of FIG. 2A, those directions along which there is a high phase contrast are tilted by 45° with respect to the xy image axes phase contrast image. By suitably forming pairs of illuminating directions 110-1-110-4, it may also be possible to generate increased phase contrast along the xy image axes of the phase contrast image. This is shown in FIG. 2B. In the scenario of FIG. 2B, the illuminating directions 110-1 and 110-2 form a first pair. The illuminating directions 110-1, 110-4 form a second pair; this means that the second illuminating direction 110-2 is assigned to two pairs. It can also be seen from FIG. 2B that a third plane 201-3 (shown in FIG. 2B by dashed lines) contains the optical axis 120. Furthermore, a fourth plane 201-4 (shown in FIG. 2B by dashed lines) contains the optical axis 120. The third plane 201-3 and the fourth plane 201-4 are oriented perpendicularly in relation to one another. The illumination vectors of the illuminating directions 110-1, 110-2 of the first pair may be transformed into one another by mirrorings of the third plane 201-3. By contrast, the illumination vectors 110-1, 110-4 of the second pair of illuminating directions may be transformed into one another by mirrorings of the fourth plane 201-4.

As can be seen from FIG. 2B, the difference vectors 115-1, 115-2 of the first and second pairs of illuminating directions 110-1, 110-2, 110-4 are oriented perpendicularly in relation to one another at an angle of 90° (cf. also FIG. 2A). At the same time, the difference vectors 115-1, 115-2 are in each case oriented parallel to the x, y image axes of the phase contrast image (unlike in FIG. 2A). The intensity images that belong to the illuminating directions 110-1, 110-2, 110-4 of a pair may in turn be combined in each case to form an original image. These original images may then be combined to form a single phase contrast image. This phase contrast image has in turn a comparatively isotropically distributed phase contrast along the various directions.

It would however also be possible to generate a first phase contrast image for the first pair of illuminating directions 110-1, 110-2 and to generate a second phase contrast image for the second pair of illuminating directions 110-1, 110-4. These two phase contrast images then have an increased phase contrast along different image directions. This may be advantageous for example in the analysis of properties of the depicted object 100. In particular, the first phase contrast image, which is determined on the basis of the first pair of illuminating directions 110-1, 110-2, has an increased phase contrast along the y image direction. Correspondingly, the second phase contrast image, which is determined on the basis of the second pair of illuminating directions 110-1, 110-4, has an increased phase contrast along the x image direction.

In FIGS. 2A and 2B, highly symmetrical cases have been shown in each case. In FIG. 2A it is possible to transform pair-forming illuminating directions 110-1-110-4 into one another by rotation about the optical axis by an angle of substantially 180°. In FIG. 2B it is possible to transform pair-forming illuminating directions 110-1-110-4 into one another by rotation about the optical axis 120 by an angle of substantially 90°. For example, in detail with reference to FIG. 2B: here the first illuminating direction 110-1 can be transformed into the second illuminating direction 110-2 by rotation about the optical axis 120 by 90° and into the fourth illuminating direction 110-4 by −90°. It would however also be possible to arrange the illuminating directions in such a way that they can be transformed into one another by some other rotational angle about the optical axis 120. Thus, it would be possible that the pair-forming illuminating directions 110-1-110-4 can be transformed into one another by rotation about the optical axis 120 by an angle other than 90° or 180°, for example an angle of greater than 25°, or preferably greater than 50°. Generally, the illumination vectors of a pair of illuminating directions 110-1-110-4 may be transformed into one another by mirroring at that plane 201-3, 201-4 that contains the optical axis 120 and has a normal vector that is oriented parallel to the corresponding difference vector 115-1, 115-2 between the respective pair-forming illuminating directions 110-1-110-4.

It is generally also not necessary that the illumination vectors of the various illuminating directions 110-1-110-4 are arranged on a circle with respect to the optical axis 120, that is to say can be transformed into one another by rotation about the optical axis 120, as is the case in the highly symmetrical case of FIGS. 2A and 2B. For example, the illuminating directions 110-1-110-4 of a pair of illuminating directions may form different angles with the optical axis 120.

Such a geometrical relationship as that which has been explained with reference to FIGS. 2A and 2B can be implemented for example by various illuminating devices that only provide a finite number of possible illuminating directions 110-1 110-4. In other words, only quite specific illuminating directions 110-1-110-4 can be realized—depending on the illuminating device. Then, for example, in each case the nearest illuminating direction 110-1-110-4 that satisfies a prescribed geometrical criterion—such as for example rotation about the optical axis 120 by a specific angle—as well as possible may be selected. This selection then satisfies the geometrical criterion within the limits of the accuracy of the illuminating device.

Figure 3:
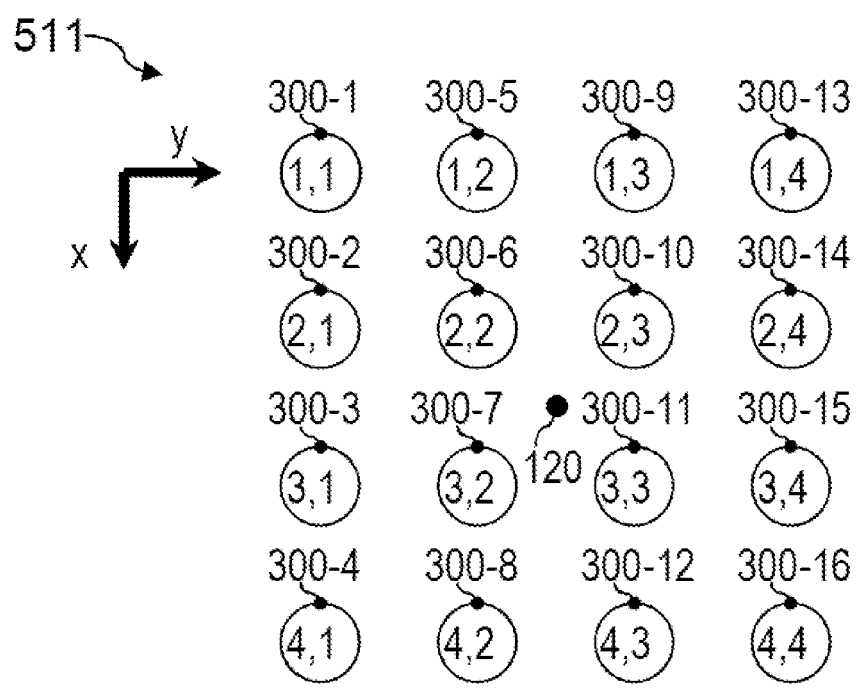
FIG. 3 schematically shows a light-emitting diode array, which can be used for illuminating an object from different illuminating directions.

In principle, it is therefore possible to use a wide variety of illuminating devices 511 for illuminating the object from the various illuminating directions 110-1-110-4. In FIG. 3, an example of an illuminating device 511 is represented in the form of a light-emitting diode (LED) array. The LED array 511 in FIG. 3 comprises 4 rows of LEDs and 4 columns of LEDs, which are arranged symmetrically with respect to the optical axis 120. In order for example to make it possible to illuminate the object 100 along the illuminating direction 110-1, the LED 300-11 may be activated. In order to make it possible to illuminate the object 100 along the illuminating direction 110-2, the LED 300-10 may be activated. In order to make it possible to illuminate the object 100 along the illuminating direction 110-3, the LED 300-6 may be activated. In order to make it possible to illuminate the object 100 along the illuminating direction 110-4, the LED 300-7 may be activated. For example, by analogy with a technique such as that represented in FIG. 2B, the following LEDs 300-1-300-16 correspond to pairs of illuminating directions 110-1-110-4: LED 300-1 and LED 300-12, LED 300-5 and LED 300-9; LED 300-2 and LED 300-14; LED 300-6 and LED 300-10; LED 300-2 and LED 300-15; LED 300-7 and LED 300-11; LED 300-4 and LED 300-16; LED 300-8 and LED 300-12. For example, the respective intensity images of a pair of illuminating directions 110-1-110-4 may be subtracted in order in each case to obtain an original image. The original images obtained in this way can then be summated in order to generate a first phase contrast image. The first phase contrast image then has a particularly high phase contrast along the x image direction.

It would correspondingly also be possible to combine the following LEDs 300-1-300-16 in each case into pairs of illuminating directions 110-1-110-4 in order to generate a high phase contrast along the y direction: LED 300-1 and LED 300-4; LED 300-5 and LED 300-8; LED 300-2 and LED 300-3; LED 300-6 and LED 300-7; LED 300-9 and LED 300-12; LED 300-13 and LED 300-16; LED 300-10 and LED 300-11; LED 300-14 and LED 300-15. In such a scenario, a first phase contrast image $DPGC_x$ can be calculated according to the following formula:

$$DPGC_x = I_1 - I_{13} + I_5 - I_9 + I_2 - I_{14} + I_6 - I_{10} + I_3 - I_{15} + I_7 - I_{11} + I_4 - I_{16} + I_8 - I_{12} \quad (1)$$

It is correspondingly possible to calculate a second phase contrast image $DPGC_y$ according to the following equation:

$$DPGC_y = I_1 - I_4 + I_5 - I_8 + I_2 - I_3 + I_6 - I_7 + I_9 - I_{12} + I_{13} - I_{16} + I_{10} - I_{11} + I_{14} - I_{15} \quad (2)$$

where $I_i$ in each case the intensity image with illumination of the object 100 from the respective illuminating direction 110-1-110-14 that corresponds to the activation of the corresponding LED 300-1-300-16.

In FIG. 3, row and column indices are also indicated for the LEDs 300-1-300-16; thus, for example, the LED 300-7 has the row index i=3 and the column index j=2. In general, to implement for example the illuminating directions 110-1-110-4 according to one of FIGS. 2A, 2B, the method may comprise: activating a first light-emitting diode 300-1-300-16 for illuminating the object from a first illuminating direction 110-1-110-4 and activating a second LED 300-1-300-4 for illuminating the object from a second illuminating direction 110-1-110-4. The first LED 300-1-300-16 then has the row index i and the column index j. The second LED 300-1-300-16 may then have the row index n−i+1 and the unchanged column index j, cf. illuminating directions 110-1, 110-2 in the scenario of FIG. 2B. The second LED 300-1-300-16 may also have the unchanged row index i and have the column index m−j+1, cf. illuminating directions 110-1, 110-4 in the scenario of FIG. 2B. It would also be possible that the second LED 300-1-300-16 has the row index n−i+1 and the column index m−j+1, cf. the pair-forming illuminating directions 110-1, 110-3 and also the pair-forming illuminating directions 110-2, 110-4 of FIG. 2A.

While in FIG. 3 a scenario in which a Cartesian grid of LEDs 300-1-300-16 was discussed, generally an other arrangements of LEDs 300-1-100-16 may be used for the LED array 511. For example, it would be possible to use a circular arrangement of LEDs 300-1-100-16 as LED array 511. It would then be possible for example in particular to implement particularly simply or particularly accurately the scenarios discussed above with reference to FIGS. 2A and 2B, in which various illuminating directions 110-1-110-4 can be transformed into one another by rotation about the optical axis 120.

Figure 4A:
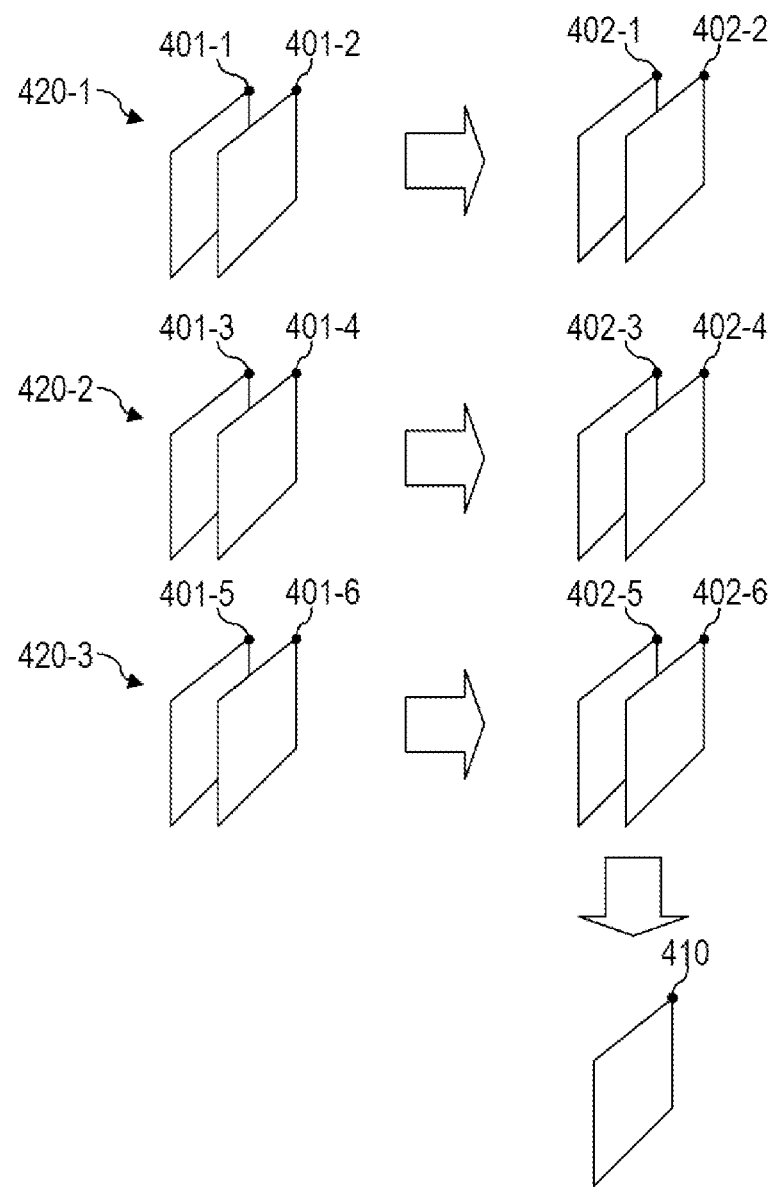
FIG. 4A illustrates a sequence for generating a phase contrast image from intensity images that have been captured while illuminating an object from various illuminating directions, an original image being generated for each intensity image, the original images being combined to generate the phase contrast image.

In FIG. 4A, the combining of intensity images 401-1-401-6 is represented. In the scenario of FIG. 4A, three pairs 420-1-420-3, which in each case consist of two intensity images 401-1-401-6, are obtained. For example, the first pair 420-1 of the intensity images 401-1, 401-2 could correspond to the illuminating direction 110-1 and the illuminating direction 110-3 (cf. FIG. 2A). In the scenario of FIG. 4A, for each of the intensity images 401-1-401-6 a corresponding original image 402-1-402-6 is determined (represented in FIG. 4A by the horizontal arrow). In a simple implementation, the original images 402-1-402-6 correspond to the intensity images 401-1-401-6. An operator may also be applied to the captured intensity images 401-1-401-6 in order to generate the original images 402-1-402-6. For example, the operator could be selected from the following group: absolute value; square; root; sign reversal; smoothing of pixels; aberration correction of pixels and normalizing to a mean value of pixel values of the respective intensity image. Then the original images 402-1-402-6 are combined to generate the phase contrast image 410. This combining may be performed for example by summation, subtraction, division or multiplication of the various original images 402-1-402-6 with one another. It is possible here for example for different original images 402-1-402-6 that correspond to different pairs 420-1-420-3 of intensity images 401-1-401-6 to be given different algebraic signs; it would correspondingly also be possible that in each case a first original image 402-1-402-6, which corresponds to a first intensity image 401-1-401-6 of a pair 420-1-420-3, is given an opposite algebraic sign in comparison with a second original image 402-1-402-6. When combining the original images 402-1-402-6, weighting factors for the individual original images 402-1-402-6 may also be taken into consideration. As a result, the influence of various original images 402-1-402-6, and consequently various illuminating directions 110-1-110-4, on the phase contrast image 410 can be controlled.

Figure 4B:
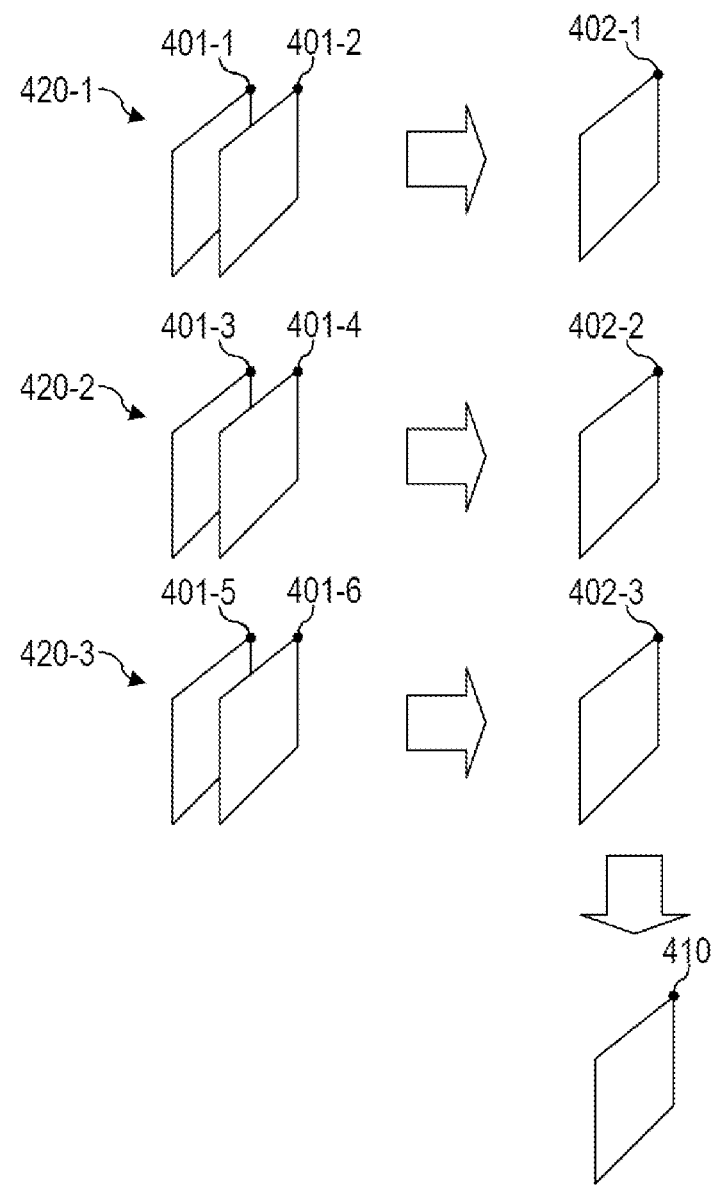
FIG. 4B illustrates a sequence for generating a phase contrast image from intensity images that have been captured while illuminating an object from various illuminating directions, the intensity images being combined as pairs to form an original image, the original images being combined to generate the phase contrast image.

In FIG. 4B, a further technique for generating the phase contrast image 410 is represented. In the scenario of FIG. 4B, in each case two intensity images 401-1-401-6 of a pair 420-1-420-3 are combined to form an original image 402-1-402-2, for example by addition, subtraction, multiplication or division. At the same time, it would be possible to apply one of the aforementioned operators to the various intensity images 401-1-401-6 or the original image 402-1-402-3 obtained in this way. Then the original images 402-1-402-3 are in turn combined in order to generate the phase contrast image 410.

While in FIGS. 4A and 4B in each case a total of six intensity images 401-1-401-6 are used, it may generally be possible to generate the phase contrast image 410 with only two intensity images 401-1-401-6.

Figure 5:
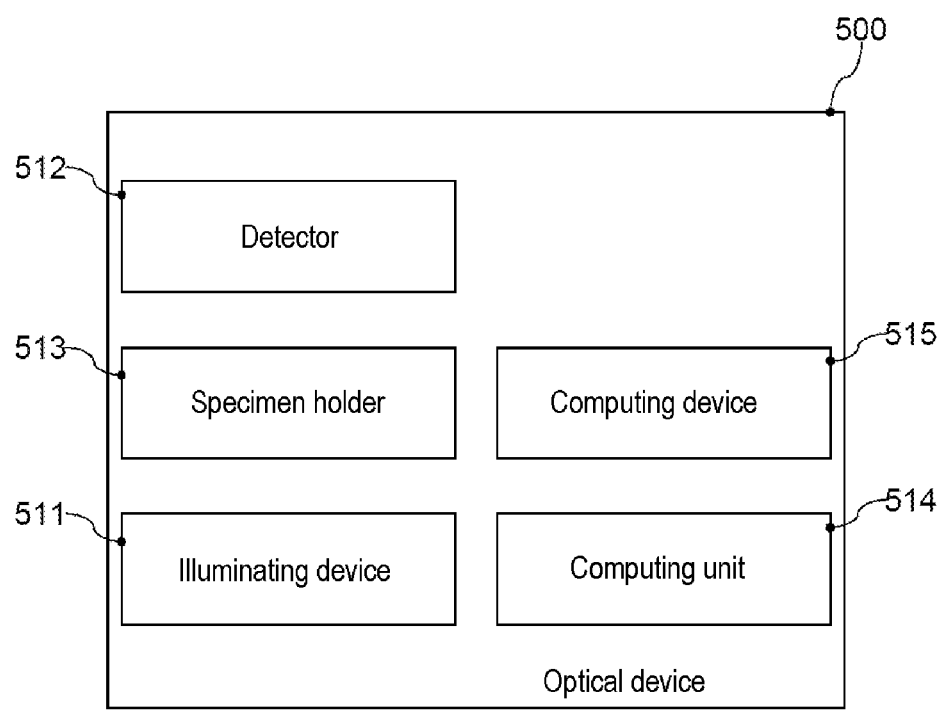
FIG. 5 schematically illustrates an optical device.

Represented in FIG. 5 is an optical device 500, with which the techniques described above can be implemented. The optical device 500 comprises an illuminating device 511, which may for example be implemented in the form of the LED array (cf. FIG. 3). The object 100 is held by a specimen holder 513 in an optical path of the light from the illuminating device 511 to a detector 512. For example, a transmission geometry in which the specimen holder 513 is arranged between the illuminating device 511 and the detector 512 may be implemented. It would also be possible to implement a reflection geometry. The optical device 500 also has a computing unit 514, which may be designed to carry out the various steps for generating the phase contrast image 410 (cf. FIGS. 4A and 4B). The optical device 500 may also have a memory 515, for example a nonvolatile memory or a volatile memory. The memory 515 may comprise corresponding items of control information for the computing unit 514, in order that the latter can execute the various techniques for generating the phase contrast image as described above.

Figure 6:
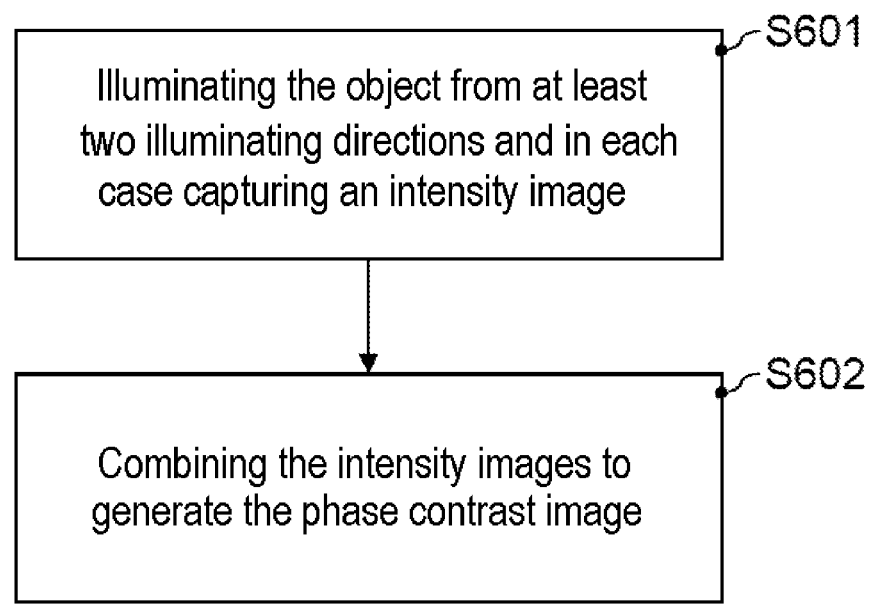
FIG. 6 is a flow diagram of a method for generating a phase contrast image.

In FIG. 6, a flow diagram of a method for generating the phase contrast image is represented. The method begins with step S601. In step S601, the object 100 is illuminated. In particular, the illuminating may be performed with incoherent light. The light with which the object 100 is illuminated in step S601 may in particular have a significant bandwidth, i.e. it may not be monochromatic. For example, the object 100 could be illuminated in step S601 with white light.

In particular, the illuminating of the object 100 in step S601 is performed from at least two illuminating directions 110-1-110-4. In step S601, the object is for example firstly illuminated from a first illuminating direction 110-1-110-4 and at the same time an intensity image 401-1-401-6 is captured. Then the illuminating of the object 100 is performed from a second illuminating direction 110-1-110-4; at the same time, a further intensity image 401-1-401-6 is captured.

In step S602, the combining of the intensity images 401-1-401-6 is performed to generate the phase contrast image 410. Various techniques may be used for the combining. In particular, weighting factors that determine an influence of the various intensity images 401-1-401-6 or original images 402-1-402-6 based on them also the phase contrast image may be determined in the combining operation. In step S602, in each case the two intensity images 401-1-401-6 of a pair may for example be combined to form an original image 402-1-402-6.

Figure 7:
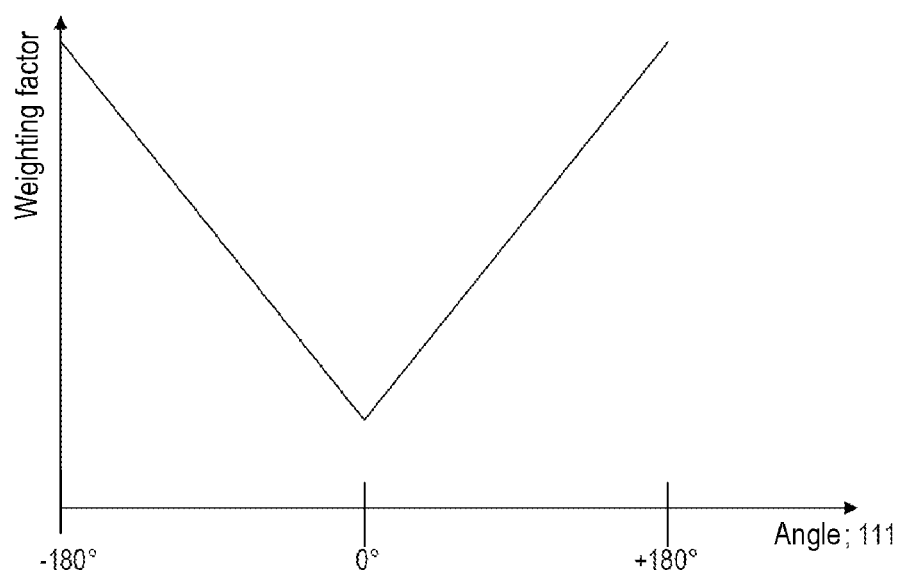
FIG. 7 shows a dependence of weighting factors on an angle of corresponding illuminating directions for the weighted summation of original images.

In FIG. 7, a dependence by way of example of the influence of the various intensity images 401-1-401-6 on the phase contrast image 410 is represented in dependence of the angle 111 that the respective illuminating direction 110-1-110-4 forms with the optical axis 120. For example, the influence of the respective intensity images 401-1-401-6 may be all the greater (smaller) the greater (smaller) the greater the absolute value of the angle 111 is.

Figure 8:
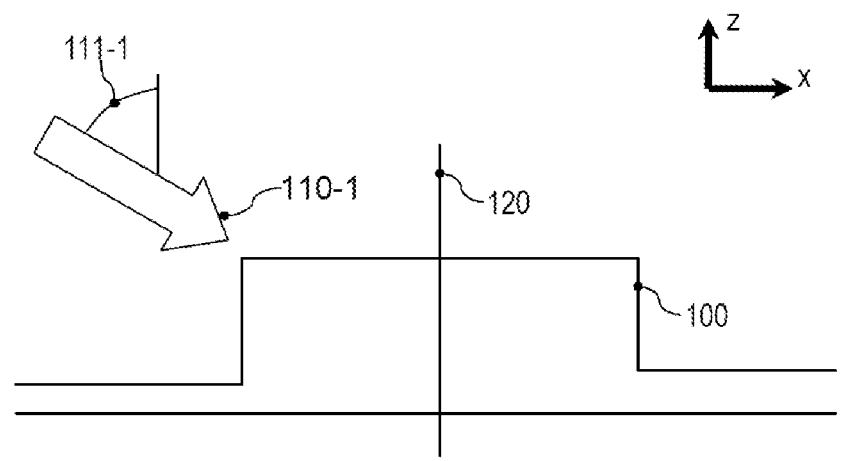
FIG. 8 illustrates the illuminating of the object from an illuminating direction that forms a finite angle with the optical axis.

In FIG. 8, a scenario in which the object 100 is illuminated from a single illuminating direction 110-1 is represented. For this purpose, for example a single LED 300-1-300-16 may be activated. It can be seen from FIG. 8 that the illuminating direction 110-1 forms a finite angle 111-1 with the optical axis 120. The object 100 in FIG. 8 has two step-shaped edges or peripheries and forms a plateau inbetween.

Figure 9:
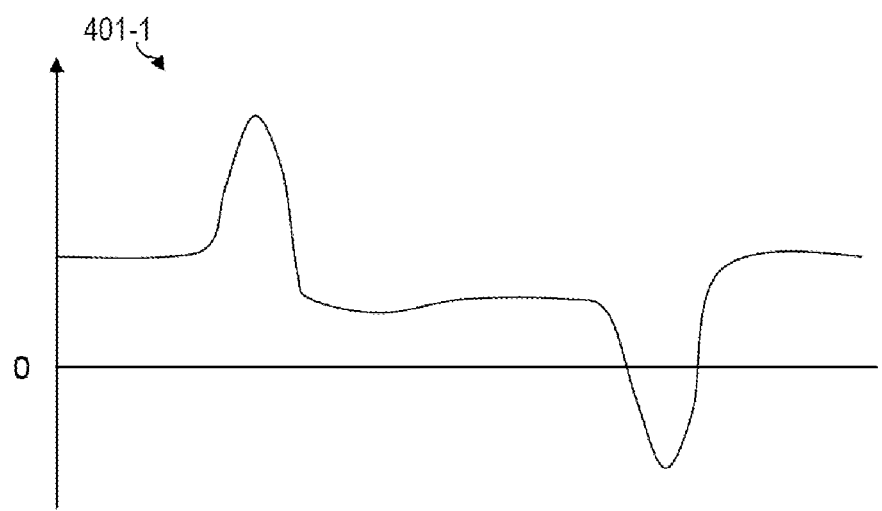
FIG. 9 illustrates pixel values of an intensity image that is captured for the illuminating direction of FIG. 8.

For the scenario of FIG. 8, a corresponding intensity image 401-1 is captured, see FIG. 9. In FIG. 9, pixel values of the intensity image 401-1 are represented in the x-z plane. It can be seen from FIG. 9 that the pixel values assume particularly great (small) values at the edge of the object 100 that is represented on the left (on the right) in FIG. 8. In the region of the plateau of the object 100, the pixel values assume substantially constant values.

Figure 10:
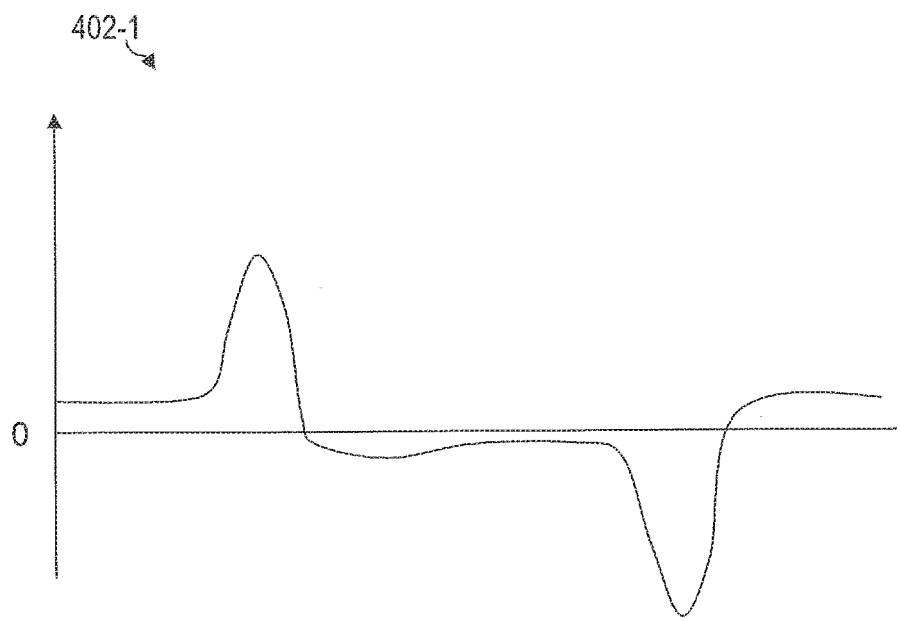
FIG. 10 corresponds to FIG. 9, the pixel values having been rescaled.

Then the intensity image 401-1 is processed in order to generate the phase contrast image 410. In FIG. 10, the rescaled intensity image 401-1 is represented and denoted as an original image 402-1. For this purpose, a mean value of the pixel values of the intensity image 401-1 is determined and this mean value is then subtracted from all the pixel values. For this reason, the curve of the pixel values is shifted downward in the representation of FIG. 10.

Figure 11:
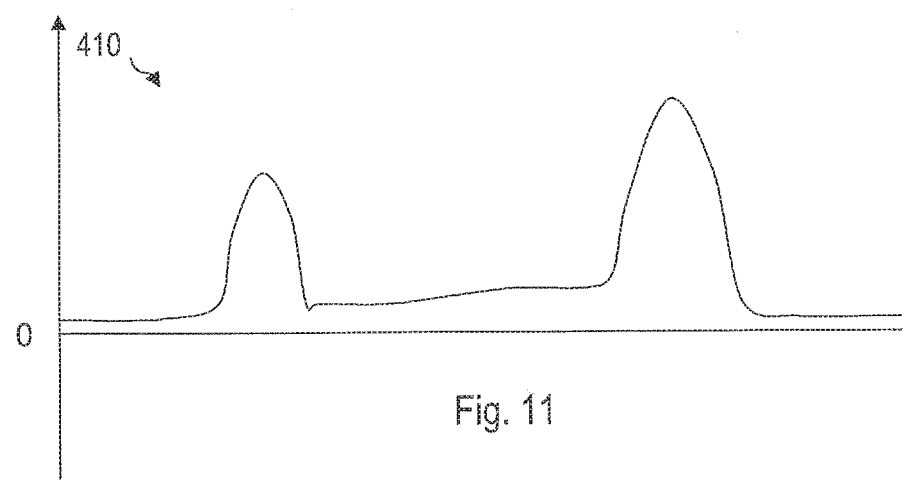
FIG. 11 corresponds to FIG. 10, an absolute value operator having been applied to the pixel values.

Then an absolute value operator, which supplies the absolute value for each pixel value, is applied to the original image 402-1. A smoothing may also be performed. As a result, the phase contrast image 410 is generated, see FIG. 11.

On the basis of such techniques, a phase contrast image 410 that has a significant phase contrast component can therefore be generated comparatively uncomplicatedly, for example just on the basis of a single intensity image 401-1-401-6. It would of course optionally also be possible to combine multiple phase contrast images 410 obtained in this way, for example for various illuminating directions 110-1-110-4, to form a resultant image, in order for example to improve the signal-to-noise ratio or obtain a more isotropic phase contrast component in the resultant image thus generated. In such a scenario, it may be superfluous that the various illuminating directions 110-1-110-4 are arranged as pairs.

To sum up, techniques which make it possible to generate the phase contrast image by specifically combining intensity images that are captured from different illuminating directions have been described. Techniques which make it possible to generate a phase contrast image by selectively processing an intensity image have also been illustrated. To this extent it is possible to speak for example of a digital phase gradient contrast. In particular, it may be superfluous to use special optical elements, such as for example prisms, etc., according to conventional techniques of phase contrast imaging.

Although the invention has been more specifically illustrated and described in detail by the preferred exemplary embodiments, the invention is not restricted by the disclosed examples and other variations may be derived therefrom by a person skilled in the art without departing from the protective scope of the invention.

The invention claimed is:

1. A method for generating a phase gradient contrast image of an object with an optical device, the method comprising the following steps:
    sequentially illuminating the object from at least two illuminating directions, by activating respective light emitting diodes (LEDs) of an LED array, wherein a distance of each respective LED from the optical axis defines the corresponding illumination direction,
    for each illuminating direction: capturing an intensity image of the object during the illumination from the respective illuminating direction,
    the at least two illuminating directions in each case being assigned to a pair of illuminating directions,
    combining, in the image space, original images which are based on the captured intensity images to generate a phase gradient contrast image of the object, and
    applying an operator to the captured intensity images to obtain the original images, the operator comprising at least one of absolute value, square, or root of pixel values of the respective intensity image.

2. The method as claimed in claim 1,
    the two illuminating directions being a pair forming correlating angles with the optical axis of the optical device.

3. The method as claimed in claim 1,
    illumination vectors of a pair of illuminating directions forming an angle with one another that is greater than 10°.

4. The method as claimed in claim 1,
    illumination vectors of a pair of illuminating directions in each case forming an angle with the optical axis of the optical device that is greater than 5°.

5. The method as claimed in claim 1,
    a first pair of illuminating directions determining a first difference vector of associated illumination vectors,
    a second pair of illuminating directions determining a second difference vector of associated illumination vectors,
    the first difference vector and the second difference vector forming an angle with one another.

6. The method as claimed in claim 5,
    the first pair of illuminating directions and the second pair of illuminating directions comprising a count of three or more illuminating directions.

7. The method as claimed in claim 5,
    the method for generating the phase gradient contrast image being used in each case for the first pair and for the second pair of illuminating directions in order to generate a first phase gradient contrast image and a second phase gradient contrast image.

8. The method as claimed in claim 1, wherein the at least two illumination directions are arranged in pairs and sequentially illuminating the object comprises:
    for each pair: activating a first LED of the LED array to illuminate the object from a first illuminating direction and activating a second LED of the LED array to illuminate the object from a second illuminating direction, the LED array having n rows and m columns,
    the first LED corresponding to the i; j LED of the LED array;
    the second LED being selected from the following group: n−i+1; j LED; i; m−j+1 LED; n−i+1; m−j+1 LED.

9. The method as claimed in claim 1,
    the method also comprising:
    combining those intensity images that correspond to a pair of illuminating directions to form in each case an original image.

10. The method as claimed in claim 1,
    the operator further being selected from the following group: smoothing of pixels; aberration correction of pixels; and normalizing to a mean value of pixel values of the respective intensity image.

11. The method as claimed in claim 1,
    the combining of the original images comprising a weighted summation of the original images, each original image being allocated a weighting factor,
    the method optionally also comprising:
    for each original image: determining the weighting factor on the basis of an angle that the corresponding illuminating direction forms with the optical axis of the optical device.

12. The method as claimed in claim 1,
    the illuminating of the object satisfying criteria that are selected from the following group:
    illuminating with incoherent light;
    illuminating with white light; and
    illuminating in such a way that the light in the optical path of the optical device between the object and a detector does not pass through any elements that are selected from the following group: pole filter; prism; Wollaston prism; phase ring; and grayscale filter.

13. An optical device, which is configured to generate a phase gradient contrast image of an object, the optical device comprising:
    an array of light emitting diodes (LEDs) configured to illuminate the object from at least two illuminating directions, by activating respective LEDs of the LED array, wherein a distance of each respective LED from the optical axis defines the corresponding illumination direction,
    the at least two illuminating directions being assigned in each case to a pair of illuminating directions,
    a detector, which is configured to capture an intensity image of the object for each illuminating direction during the illumination from the respective illuminating direction, and
    processing circuitry, which is configured to combine original images based on the captured intensity images in the image space to generate a phase gradient contrast image of the object, wherein the computing unit is configured to apply an operator to the captured intensity images to obtain the original images, the operator comprising at least one of absolute value, square, or root of pixel values of the respective intensity image.

* * * * *